United States Patent [19]

Ankeny et al.

[11] Patent Number: 5,161,407
[45] Date of Patent: Nov. 10, 1992

[54] MEANS AND METHOD OF SOIL WATER DESORPTION

[75] Inventors: Mark D. Ankeny, Ames, Iowa; Hugh J. Brown, Cambridge, Vt.; Richard M. Cruse, Ames, Iowa

[73] Assignee: Iowa State University Research Foundation, Inc., Ames, Iowa

[21] Appl. No.: 598,256

[22] Filed: Oct. 16, 1990

[51] Int. Cl.$^5$ .................................. G01H 15/08
[52] U.S. Cl. .................................................. 73/38
[58] Field of Search .................. 73/38, 73, 76, 866

[56] References Cited

U.S. PATENT DOCUMENTS

| | | | |
|---|---|---|---|
| 966,078 | 8/1910 | Bowman | 73/38 |
| 2,534,718 | 12/1950 | Leas et al. | 73/38 |
| 2,540,096 | 2/1951 | Bull | 73/38 |
| 2,612,036 | 9/1952 | Angona | 73/38 |
| 2,676,485 | 4/1954 | Morgan | 73/38 |
| 3,103,117 | 9/1963 | Richards | 73/73 |
| 3,871,211 | 3/1975 | Tal | 73/73 |
| 3,884,067 | 5/1975 | Mottes | 73/73 |
| 3,898,872 | 8/1975 | Skaling et al. | 73/73 |
| 3,910,300 | 10/1975 | Tal | 137/78 |
| 4,478,069 | 10/1984 | Zuckerwar | 73/38 |
| 4,520,657 | 6/1985 | Marthaler | 73/73 |
| 4,884,436 | 12/1989 | Ankeny et al. | 73/38 |
| 4,970,169 | 11/1990 | Sanders | 73/38 |

FOREIGN PATENT DOCUMENTS

1286956  1/1987  U.S.S.R. .................. 73/38

OTHER PUBLICATIONS

Moore, Burch and Wallbring, "Preferential Flow and Hydraulic Conductivity of Forest Soils", *Soil Sci. Soc. Am. J.*, pp. 876–881, vol. 50, 1986.

Constantz and Murphy, "An Automated Technique for Flow Measurement From Mariott Reservoits," *Soil Sci. Soc. Am. J.*, pp. 252–254, vol. 51, 1987.

Clothier and White, "Measurement of Sorptivity and Soil Water Diffusivity in the Field," *Soil Sci. Soc. Am. J.*, pp. 241–244 vol. 45, 1981.

*Primary Examiner*—Robert Raevis
*Attorney, Agent, or Firm*—Zarley, McKee, Thomte, Voorhees & Sease

[57] ABSTRACT

A soil desorption device and method which utilizes an easily manufacturable and assemblable pressure cell to contain soil samples. The pressure cells are in turn easily attachable to pneumatic pressure manifolds and can be independently valved. The cells are also easily adapted to be connected to collection containers for any desorbed fluid. Each cell utilizes a cylindrical container having rubber gaskets at opposite ends and which can be sandwiched between top and bottom plates to seal the container. A thin nylon membrane having small pores is positioned at the bottom of the container and the bottom plate has apertures to allow fluid forced through the membrane to pass to the fluid collection devices. This cell presents low impedance to fluid flow, produces high flow rates, and allows maintenance of good seals and accurate pressurization of each cell. These and other features and advantages allow for more economical and better soil desorption procedures and soil hydraulic characteristic measurements.

29 Claims, 2 Drawing Sheets

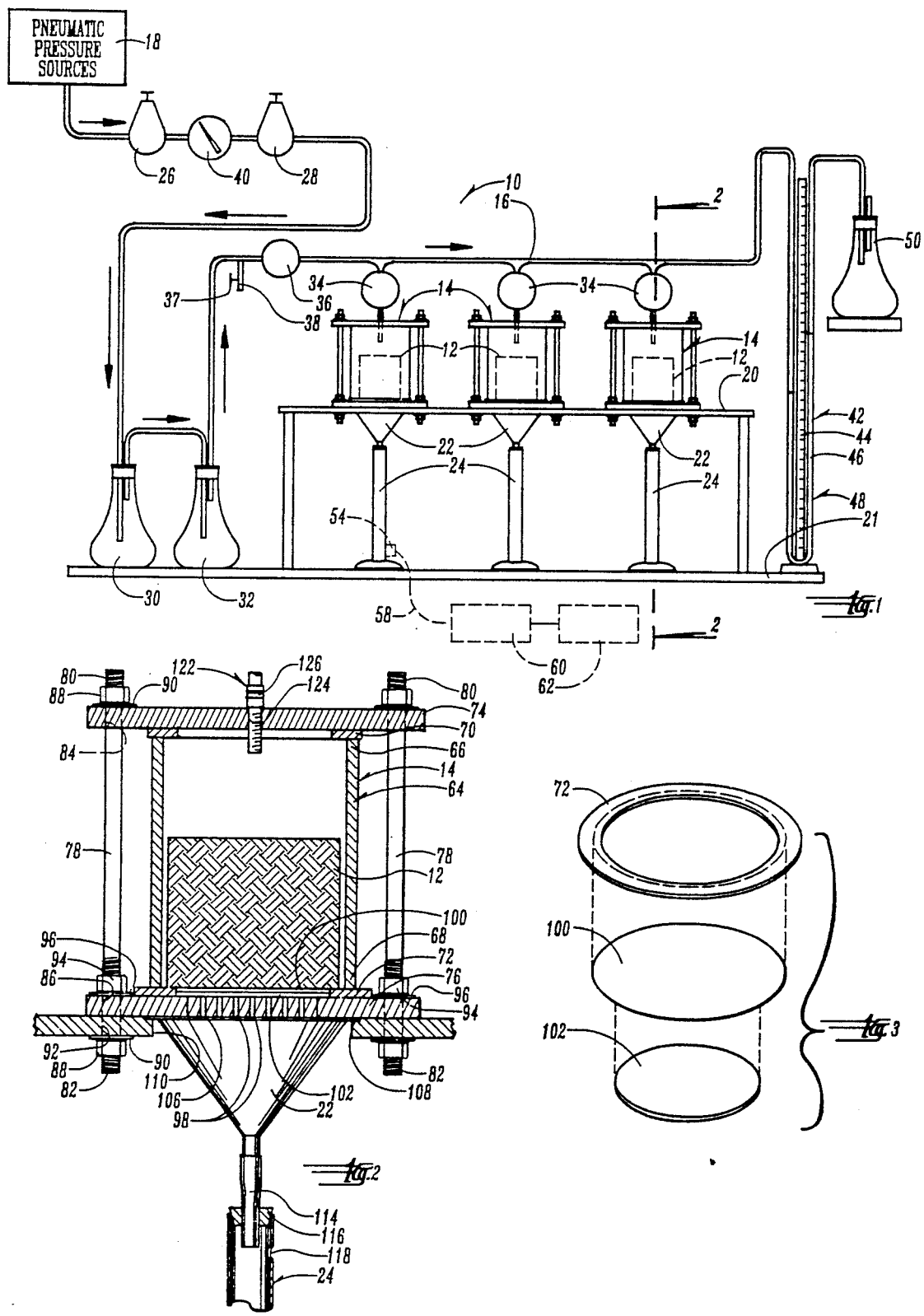

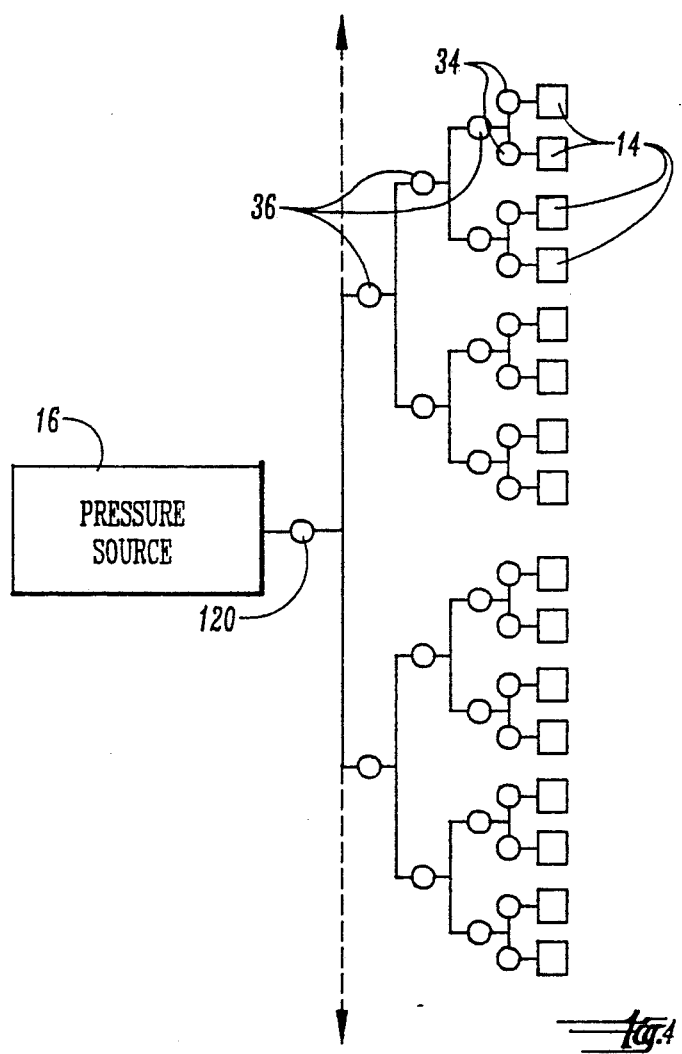

MEANS AND METHOD OF SOIL WATER DESORPTION

BACKGROUND OF INVENTION a. Field of Invention

The present invention relates to means and method for desorbing water from soil samples, and in particular, relates to an improved structure and method for performing such procedures, either with a single soil sample, or with multiple soil samples.

b. Problems in the Art

The uses and advantages of soil water desorption are well known within the art. Such procedures allow hydraulic characteristics of soil samples to be derived and studied.

This type of analysis is valuable in agriculture, agronomy, and environmental applications, to name but a few. A specific example is the study of how agricultural machinery traffic over the soil can affect its ability to transport and store water, which in turn impacts on crop production.

The process of water desorption is defined as removing sorbed substances by the reverse of adsorption or absorption. In order to test soil characteristics such as the porosity of the soil (which in turn can determine how it can handle and store water), one procedure which is utilized to desorb water, is to take the soil sample (which has at least some sorbed water in it), and place it in a container which can be pressurized (called pressure cells). The container has some means (generally one end or wall) which serves as a filter in the sense it allows only passage of water when the container is raised to a certain air pressure. The amount of air pressure needed to force the corresponding amount of water from the soil sample is then utilized to understand the energy state at which that amount of water was held by the soil sample. This in turn can be converted into an understanding of the structure or hydraulic characteristics of the soil.

Described another way, soil generally is a complex composition of soil particles and pores or channels. This allows soil to adsorb and absorb water, as well as transport water through the soil in response to certain pressures.

By widely known physical properties, water adheres to pores and channels in the soil. This "adhesion force" must be overcome by some other force or energy to remove the water from the pores or channels. Therefore, procedures have been used applying known quantities of air pressure to soil samples and correlating the amount of water removed from the pressure cell to the adhesion force for that water in the soil. Then predictions and estimations are made of what the structure of the soil sample is to create that amount of adhesion force.

Some presently conventional structures utilized for soil water desorption are Buchner funnels, Tempe cells, and tension tables. These are well known to those of ordinary skill in the art. While these methods and structures are widely used, it has been found that each has limitations and deficiencies. A real need in the art exists for advancement and improvement in the means and methods used for soil water desorption.

For example, Buchner funnels and Tempe cells are costly and somewhat fragile. They also generally utilize ceramic or fritted glass plates as filters and therefore are subject to plugging. These sorts of concerns illustrate the room for improvement which exists with these devices concerning economy, reliability, and efficiency.

Tension tables are relatively inexpensive but also have deficiencies. First of all, they utilize only lower pressure potentials. Also, their structure requires constant vigilance and frequent maintenance to prevent entry of air into the system.

As is known in the art, pressure cells require that a portion or wall of the cell be sealed off by filter material that under super-atmospheric pressure of sufficient value allows the water to be forced through the pores in the material. In conventional pressure cell systems such material has been, for example, ceramic plate, fritted glass, glass beads, sand, and silt.

Significant problems exist with maintaining a sufficient difference in air pressure between the inside of the pressure cell and the outer side of the filter to allow sufficient pressure differentials to move all the water or at least most of the water out of the soil sample and cell. Obviously, such materials as glass beads, sand, and silt are relatively loose porous materials, whereas ceramic plate and fritted glass are tight, rigid, and can have very small pores. As can be appreciated, the former three substances allow fairly easy passage of water at minimum pressure differentials, but would not allow high pressure differentials to be maintained. No satisfactory material has been found for economical and flexible use with soil desorption.

One known attempt has been made to utilize a considerably different material for the filter. E. L. McCoy, in "Wettable Porous Plastic For Use As A Porous Barrier In Soil Hydraulic Studies", Soil Sci. Soc. Am.J. 53:979–981 (1989) discusses utilizing two porous plastic sheets within a Tempe cell. The advantages found with this material were high water conductance rates (on the order of 0.2 per hour). A significant problem, however, is that the unit is very costly.

It is therefore a principal object of the invention to provide a means and method for soil water desorption which solves or overcomes the problems and deficiencies in the art.

A further object of the present invention is to provide a means and method as above described which allows pressure cells to be pressurized over a wide and sufficient range for various soil water desorption processes.

Another object of the present invention is to provide a means and method as above described which has a structure which is easily disassemblable to allow insertion of soil samples and filters, and yet can be reliably sealed to deter air leaks while in use.

A still further object of the present invention is to provide a means and method as above described which is extremely economical with respect to its parts and to its manufacture.

Another object of the present invention is to provide a means and method as above described which is flexible in how it can be made as far as size, configuration, and positioning.

Another object of the present invention is to provide a means and method as above described which provides low impedance to fluid flow and therefore high flow rates through the filter.

A still further object of the present invention is to provide a means and method as above described which can be used with one pressure cell or with multiple pressure cells or sets of pressure cells.

Another object of the present invention is to provide a means and method as above described which is easily adaptable to a number of different implementations and uses for soil desorption processes and procedures.

Another object of the present invention is to provide a means and method as above described which is efficient, reliable, durable, and economical.

These and other objects, features, and advantages of the present invention will become more apparent with reference to the accompanying specification and claims.

SUMMARY OF THE INVENTION

The present invention relates to a soil water desorption device and system. It utilizes a non-complex, but easily manufactured and assemblable pressure cell for holding a soil sample to be studied.

Each pressure cell consists of basically a tubular container having opposite open ends. The top and bottom plates are sealed by gaskets to the opposite open ends by securing means which sandwich the container and gaskets to the opposite top and bottom plates. Additionally, the bottom plate includes apertures aligned with the bottom open end of the tubular container. Also, a porous membrane comprising the filter is secured between the bottom plate and the soil sample which is placed in the container. The membrane is aligned with the apertures in the bottom plate.

A conduit to a pneumatic pressure source extends through the top plate into the interior of the container. A fluid collection means is mounted directly below the apertures through the bottom plate. The fluid collection means is maintained at atmospheric pressure so that superatmospheric pressure can be set up inside the soil sample holding container. The structure of the pressure cell minimizes and deters any air leaks. This assists in the reliability of the desorption process and any correlation measurements, as well as contributes to uniformity between pressure cells.

The filter used in the present invention is a nylon membrane of quite small thickness and with small micrometer diameter pores. This combination allows for good flow rates because of low fluid-flow impedance.

The invention also allows for economical and efficient installation of one or more of the pressure cells to the system for sequential or simultaneous desorption of one or multiple soil samples. The system utilizes individual valving for each cell, or valving of sets of cells towards this purpose. This also allows easier isolation of air leak problems by allowing selective isolation of sets and subsets of cells until any leak problems can be found.

Other features and options will be discussed in more detail hereafter. It can be seen that the invention achieves at least all of its stated objectives. It reduces the complexity and high cost of conventional soil water desorption devices while increasing reliability and flexibility for these procedures.

BRIEF DESCRIPTION OF THE DRAWINGS

FIG. 1 is a diagrammatic elevational view of the system according to the present invention.

FIG. 2 is an enlarged cross sectional view of one of the pressure cells of FIG. 1.

FIG. 3 is an exploded perspective view of a sealing gasket, nylon membrane filter, and nylon mesh spacer which can be used with a preferred embodiment of the invention.

FIG. 4 is a diagrammatic representation of the provision of pressurized air and individual valving of a plurality of sets, subsets, and individual pressure cells, according to an embodiment of the present invention.

DETAILED DESCRIPTION OF THE PREFERRED EMBODIMENT

To assist in an understanding of the invention a detailed description of a preferred embodiment of the invention will now be set forth. It is to be understood that this description does not and is not intended to specifically limit the invention, but rather illustrates the specific forms and embodiments the invention can take.

To further assist in this description, reference will be taken to the drawings identified as FIGS. 1-4. Reference numerals will be used to indicate parts or locations in the drawings. The same reference numerals will be used to identify the same parts or locations in each of the drawings unless otherwise indicated.

Previously, basic uses for water soil desorption devices and methods have been discussed. The present invention provides an improved water desorption device and method which can be used flexibly for many different processes and procedures, particularly related to the study of soil samples.

Reference can also be taken to co-owned U.S. Pat. No. 4,884,436 to Ankeny, et al., issued Dec. 5, 1989, for additional discussion of means and method for analyzing hydraulic characteristics of soil. This patent is incorporated by reference to this description.

With particular reference to FIG. 1 of the drawings, a soil water desorption system 10 is shown. Three different soil samples 12 are positioned in separate pressure cells 14. A pneumatic pressure manifold 16 supplies pressurized air to each cell 14 from a pneumatic pressure source 18.

Cells 14 are mounted to what will be called table 20. FIG. 1 shows that the entire system 10 must sit on some kind of a base or floor 21. Beneath each cell 14 is a collection funnel 22 which drains any collected water into a collection cylinder 24.

The pressurized air from pneumatic pressure source 18 (in the preferred embodiment either an air compressor or portable tank), is stepped down with a primary pressure regulator 26. A secondary pressure regulator 28 is then adjustable to selectively control the level of air pressure to manifold 16. A pressure gauge 40 is also utilized as shown in FIG. 1.

In the preferred embodiments, manifold 16 is a low pressure manifold in the range of 0-350.0 kPa (kilo Pascals—an absolute unit of pressure convertible to centimeters or meters of $H_2O$). It is available from Soil Test, 86 Albrecht Drive, Lake Bluff, Ill. 60644.

Also, in the preferred embodiment, pneumatic pressure to manifold 16 is first routed through a water trap 30, and a humidifying flask 32 (both Erlenmeyer flasks). Water trap 30 can be utilized as a protective device to prevent any possibility of back up of water through manifold 16 to regulators 26 and 28 and as a protection device into pneumatic pressure source or system 18. Humidifying flask 32 is utilized to provide a minimum level of humidity to the pneumatic pressurized air to prevent drying out of the soil samples because many times, the pneumatic pressure source 18 utilizes dehumidified air to prevent corrosion or rusting of pipes or structure.

FIG. 1 specifically shows that the branch of manifold 16 which enters into each cell 14 contains a valve 34

(shown schematically). Each valve 34 can be independently operable to close or open that particular parallel manifold pathway. System 10 can therefore be used for one, two, or three pressure cells 14. Additionally, a valve 36 can be placed directly in manifold 16 and can be utilized to open or close the entire manifold 16 to the entire set of cells 14. It is also to be understood that a relief valve 37 (with a manual closure), indicated by branch 38 which is vented to atmosphere, could be used. This could allow any excess pressure to bleed from the system when changing the pressure settings.

A nonessential portion of system 10 is the manometer 42 shown on the right side of FIG. 1. Manometer 42 can be utilized to verify or calibrate pneumatic pressure within manifold 16. Manometer 42 utilizes, such as known in the art, a calibrated meter stick 44 and mercury 46 within tubing 48. It can include a mercury trap 50 at the end of the pneumatic line.

FIG. 1 also diagrammatically depicts an additional optional feature that could be utilized with any or all of the collection cylinders 24. A pressure transducer 54, such as known in the art, could be incorporated at the bottom of cylinder 24. This transducer 54 monitors and creates an electrical signal which has been calibrated to correlate with the relative pressure at each location within cylinder 24. As can be shown, wire 58 communicates these electrical signals to a processor 60 which stores and/or records the measures. Such information could be in turn be sent to a computer 62 which can compile these readings in conjunction with other parameters, such as incremental changes in pressure from the pressure source 18. As is known in the art, pressure in cylinder 24 can be converted into a precise reading of how much fluid is within cylinder 24. Reference can be taken to incorporate by reference U.S. Pat. No. 4,884,436 for discussion of this type of automated monitoring. This, therefore, can be used as a means of precisely and automatically monitoring how much water is being forced out of each pressure cell 14 at what point in time. This can then be correlated with the amount of pressure in each cell 14, which in turn can be used to derive how much force it has taken to push that amount of water from each cell 14. This finally can be used to estimate the hydraulic properties and structural characteristics of each soil sample 12.

It can therefore be seen that the comprehensive system shown in FIG. 1 can be used to perform soil desorption processes on one or more soil samples. In the preferred embodiment, the structures utilized are non-complex, and easy to assemble and use. If there is an available pneumatic pressure source, the system, even for multiple and simultaneous soil samples, is extremely inexpensive and economical. As shown, it can easily also be automated. Pressure readings, and other relative monitors can be used to completely automate collection of the relative parameters which are changed during the course of the desorption processes. These monitors and transducers can then be hooked into the processor 60 and/or computer 62 to perform automated calculations with appropriate software instructions.

FIG. 2 shows in greater detail the exact structure of the preferred embodiment of pressure cell 14. A 102 millimeter in diameter circular acrylic tube 64 is positioned vertically to form the holding container for soil sample 12. The top and bottom edges 66 and 68 of tube 64 are sealed against rubber ring gaskets 70 and 72 respectively, which in turn are sealed against the flat interfacing surfaces of top plate 74 and bottom plate 76 respectively. Top and bottom plates 74 and 76 ca be 12.7 millimeter thick polycarbonate plates having outside dimensions which are greater than the outside diameter of tube 64.

A plurality of rods or bolts 78, having opposite threaded ends 80 and 82, are insertable through corresponding apertures 84 and 86 in top and bottom plates 74 and 76 respectively. Nuts 88 and washers 90 are used to bring top and bottom plates 74 and 76 towards one another to essentially sandwich tube 64 against gaskets 70 and 72.

In the particular embodiment of FIG. 2, rods or bolts 78 also extend through apertures 92 in table 20 and have additional nuts and washers 94 and 96 threaded into position on the inner side of bottom plate 76 between top plate 74 and bottom plate 76. This combination allows not only the sandwiching of tube 64 between top and bottom plates 74 and 76 but also allows each cell 14 to be securely mounted to table 20. Moreover, after mounting to table 20, it allows quick and easy removal of top plate 74 to insert and remove various soil samples 12, without having to remove or disassemble cell 14.

FIG. 2 furthermore shows that a plurality of apertures 98 extend between opposite surfaces of bottom plate 76, basically in alignment with the bottom open end of tube 64. A combination of a nylon membrane filter 100 and a nylon mesh spacer 102 are also sandwiched between the bottom of tube 64 and the innerfacing surface of bottom plate 76. Specifically, the nylon membrane filter 100 is compressed between bottom plate 76 and gasket 72. The nylon mesh spacer 102 can simply be positioned between bottom plate 76 and membrane filter 100 and serves to allow atmospheric air through apertures 98 to come into contact with substantially all the bottom of nylon membrane filter 100.

FIG. 2 also shows that in the preferred embodiment, a conical funnel 22 having a lip 106 can be mounted immediately underneath and surrounding apertures 98 of bottom plate 76 by placing lip 106 in notch 108 machined around pre-existing hole 110 in the top of table 20. Funnel 22, in turn, drains into calibrated collection cylinder 24.

It is to be understood that in FIG. 2, a preferred embodiment of the junction between funnel 22 and cylinder 24 is shown. Instead of having funnel 22 directly extend into cylinder 24, a flexible hose 114 is attached to the bottom of funnel 22 and routed to a stopper 116 in the neck of cylinder 24. This allows the cylinders 24 to be easily disconnected from the funnels 22, which are secured in place so that cylinders 24 can be removed, weighed, and reinstalled without lifting of table 20 or other difficult procedures.

It is noted that the upper portion of cylinder 24 contains a pin hole (exaggerated in size in FIG. 2) to maintain atmospheric pressure in cylinder 24, and subsequently in funnel 22. Stopper 116 is utilized to deter and limit evaporation from cylinder 24. It is essential for the operation of the invention that atmospheric pressure be maintained immediately below nylon membrane filter 100 so that a positive pressure potential can be set up between the interior of cell 14 and that lower side of membrane filter 100.

In the preferred embodiment of FIG. 2, nylon membrane filter 100 is available from Micron Separations Inc., of 135 Flanders Road, Westboro, MA 01581. As previously mentioned, the size of pressure cells 14 can be varied. Therefore, nylon membrane filters 100 can also be varied according to size of cell 14 and particular application.

For example, the nylon membrane filters 100 can have pores ranging from 0.22 micrometers to 5.0 micrometers in pore diameter, can range from 13 to 293 millimeters in overall diameter and can be of various thicknesses. However, in the preferred embodiment, the filters are generally very thin, 120 micrometers in thickness or less, are hydrophilic, have high flow rates, and are resistant to most organic solvents. The size of tubes 64 of pressure cell 14 can be selected according to desire or requirement for certain soil water desorption processes. One example would be at 102 millimeter diameter which would allow a 76 millimeter Uhland core to be desorbed.

In the preferred embodiment apertures 98 are 3.2 millimeter holes drilled in three concentric circles with radii of 20, 40, and 60 millimeters from the center of the bottom plate 76.

The nylon mesh spacer 102 allows the flow of water between nylon membrane filter 100 in bottom plate 76. Rods 78 are 6.35 millimeter diameter bolts secured with hexagonal nuts 88.

It is to be understood that gaskets 70 and 72 eliminate the need of many conventional systems to utilize of lubricants or vacuum grease for sealing. This, therefore, also eliminates some cost and complexity in the assembly and maintenance of the system.

Funnel 22 can be made of polyethylene. Graduated cylinders 24 are weighable to an accuracy of 0.01 gram.

FIG. 3 shows in exploded perspective format, the preferred embodiment of the lower gasket 72, nylon membrane filter 100, and nylon mesh spacer 102. It is to be understood that in this preferred embodiment, the inner diameter of gasket 72 is 4 inches, and the outer diameter is 4½ inches. The outer diameter of membrane 100 is 4½ inches, allowing its outer perimeter to be clamped down on to bottom plate 76 by gasket 72. Additionally, it is to be understood that the innerfacing surfaces of both top and bottom plates 74 and 76 can contain indicia o markings to facilitate alignment of gaskets 70 and 72 in their appropriate centered position. Moreover, in the preferred embodiment, upper gasket 70 can be glued into position to eliminate the need to hold it in a centered position during assembly.

Also in the preferred embodiment, nylon mesh spacer is approximately 3 inches in diameter. It is made of a highly porous material (approximately 15 holes per linear inch) to allow water to easily flow between membrane 100 and bottom plate 76, and facilitate the presure differential on opposite sides of membrane filter 100. Without it, membrane filter 100 would be pressed directly over apertures 98 and bottom plate 76 which would not allow a uniformity of pressure along membrane 100 or water to spread across the bottom of membrane 100.

FIG. 4 simply diagrammatically shows how system 10 could be configured to allow selective operation of many pressure cells 14 simultaneously. The pressure source 18 could be connected to a main manifold control valve 120. In turn, branches of the system could spread out to an unlimited number of pressure cells 14. The advantage of such a system is that the valves and tubing required for such are not very expensive, and it allows not only each cell 14 to be individually turned on or off but allows each set of two or four cells 14, for example, to be turned on or off as well as each preceding set. This is particularly advantageous when checking for air leaks or preforming other maintenance. The number of cells 14 which can be used with such a system is theoretically unlimited. For example, a hundred cells 14 are envisioned to be practicable with this system.

Set up begins with gathering parts for an appropriate number of cells 14, collection funnels and cylinders 22 and 24. An appropriate supporting table 20, manifold 16, valves 34, 36, and any automated transducers and processors are selected, as desired. The pneumatic pressure source 18 with appropriate pressure regulators, water traps and humidifying devices, as desired, are also selected.

Next, the rods or bolts 78, funnels 22, and bottom plate 76 can then be installed on to table 20 using nuts and washers, 88, 90, 94, and 96. Gasket 72 and membrane filter 100 and mesh spacer 102 can then be positioned on bottom plate 76. Tube 64 can then be positioned over gasket 72, and a soil sample can be put into each tube 64.

Top plate gasket 74, with gasket 70 preferably previously glued and centered to its top inside surface, can then be positioned over rods 78 and tube 64. Top nuts 88 can then be turned down to sandwich and secure the cell 14 into a sealed position.

It is noted that a fitting 122 (see FIG. 2) can be utilized to connect the interior of cell 14 to pressure manifold 16. Fitting 122 can be threaded through a threaded aperture 124 through top plate 74 and can have a standard tube fitting 126 which can be used with appropriate clamps or rings to seal the tubing of manifold 16 to fitting 122.

In operation, it is to be understood that before placing soil samples 12 into pressure cells 14, the system should be checked for air leaks at the highest pressure potential which will be used. After that test, the entire system can be left in place except for the quick and easy removal of top plates 74, insertion of soil samples, and then reinstallation of top plates 74.

It is also to be understood that in the preferred embodiment, it is generally preferred that de-aired water be used when hydrating or soaking soil sample 12. This helps in the removal of air from the pores of the sample. Once this is all in place, the desorbing procedure can be operated according to different methods.

For example, the system 10 can be used for one-step outflow procedures (see for example Kool, et al. 1985, Determining Soil Hydraulic Properties From One-Step Outflow Experiments By Parameter Estimation I. Theory and Numerical Studies. Sci. Soc. Am. J. 49:1348-1353). Alternatively, as previously mentioned, the positive pressure potential could be applied to cell 14 and then the amount of water draining from the soil sample into collection cylinder 24 could be measured for each incremental increase in pressure.

It is also to be understood that for an initial draining curve (see or example Klute, 1986, Water Retention: Laboratory Methods in. Klute (ed.) Methods of Soil Analysis. Part 1. Second Ed. Agronomy 9:377-382), funnel 22 could be stoppered and filled with de-aired water. A vacuum could then be applied to manifold 16 causing water to be drawn up from cylinder 24 to wet the soil sample 24 from below.

By further example, to obtain a main drainage curve, water can simply be added to cell 14 to some depth, top plate 72 can be bolted in place and then allowed to be drained from the system under regulated pressure.

The included preferred embodiment given above is by way of example only, not by way of limitation to the invention, which is solely described by the claims herein. Variations obvious to one skilled in the art will be included within the invention defined by the claims.

The performance of soil water desorption according to the present invention compares favorably to conventional techniques. Additionally, the present invention has average flow rates significantly higher than conventional techniques. It is believed that the thin thickness nylon membrane filters 100, in spite of smaller pore diameters than conventional ceramic or fritted glass disks, has less impedance or resistance to water flow. Advantages of such lower impedance have been previously described. By way of further example, the higher flow rates allow estimation of hydraulic conductivity-water potential function in conjunction with measurement of a water retention characteristic. Soil water diffusivity can also be calculated from one-step outflow experiments made possible with this invention. See Valintezas, J.D. 1989. A Simple Approximate Equation To Calculate Diffusivities From One-Step Outflow Experiments. Soil Sci. So. J. 53:342-349.

Also, since the rate of flow is time dependent, reducing the impedance of the soil water desorption device may improve the accuracy of the estimation of hydraulic conductivity or hydraulic defusivity.

An optional feature, which can be incorporated into the invention to assist accurate assembly of each pressure cell 14, could be the use of enlarged diameter washers 96 used in conjunction with nuts 94 as shown in FIG. 2. If washers 96 are enlarged, they could be selected of a size which would automatically center gaskets 72 and eliminate the need for approximate centering or the indicia marked on the surface of bottom plate 76 to accomplish such centering.

The tubing associated between funnel 22 and cylinder 24 FIG. 2 can be Tygon ™ tubing.

Finally, the present system can be used to establish pressure potentials of up to about 10.0 meters of water.

What is claimed is:

1. A soil desorption device comprising:
    a hollow container defining a chamber for holding an at least partially hydrated soil sample, the container having top and bottom edges defining open top and bottom ends;
    a top plate closable over the open top end;
    a bottom plate closable over the open bottom end;
    a top plate closable over the open top end;
    a bottom plate closable over the open bottom end;
    elastromeric gasket means insertable between and for providing a fluid-tight seal between the top and bottom plates and the top and bottom edges respectively;
    thin nylon membrane filter means insertable between the soil sample and the bottom plate for providing low impedance, high rate water flow, while maintaining sufficient pressure differentials between inside and outside of the container over a wide range of pressures, the nylon membrane filter means having pores with pore diameters ranging from 0.22 micrometers to 5.0 micrometers;
    locking means for securing the top and bottom plates to the open top and bottom ends of the container to substantially seal the container;
    the bottom plate including apertures which are coincident with the nylon membrane filter means;
    collection means positioned adjacent the bottom plate around the apertures opposite the nylon membrane filter means for collecting any water passing through the apertures of the bottom plate, the collection means including means for maintaining the collection means at atmospheric pressure;
    conduit means for supplying communication between a pressurized air source and the soil sample chamber, to allow pressurization of the chamber to levels which force any free water and at least some of any absorbed or adsorbed water in the soil sample through the nylon membrane filter means to the collection means.

2. The device of claim 1 wherein the hollow container comprises a tubular cylinder having a circular cross section.

3. The device of claim 2 wherein the hollow container is made from an acrylic material.

4. The device of claim 1 wherein the top and bottom plates have substantially flat top and bottom surfaces.

5. The device of claim 4 wherein the top and bottom plates are made of polycarbonate material.

6. The device of claim 1 wherein the elastomeric gasket means consists of rings substantially coinciding with the top and bottom edges of the hollow container and being made of a rubber material.

7. The device of claim 1 wherein the nylon membrane filter means include a plurality of pores, are hydrophilic, and are resistant to organic solvents.

8. The device of claim 8 wherein the nylon membrane filter means has pores with pore diameters generally ranging from 0.22 micrometers to 5.0 micrometers and, the nylon membrane filter means is from 13 to 293 millimeters in overall diameter.

9. The device of claim 8 wherein the nylon membrane filter means has pores with an average pore diameter of approximately 0.45 micrometers.

10. The device of claim 1 wherein the locking means comprises securement means connected between the top and bottom plates which can allow removal of either the top and bottom plate and which can allow tensioning of the top and bottom plates to one another.

11. The device of claim 1 further comprising support means for supporting the device.

12. The device of claim 1 wherein the apertures through the bottom plate consist of a plurality of holes generally uniformly spaced apart around the center of the bottom plate.

13. The device of claim 12 wherein the apertures are substantially larger than the pores of the nylon membrane filter means, and are spaced from the nylon membrane filter means.

14. The device of claim 1 wherein the collection means consists of a funnel means mountable directly beneath the apertures of the bottom plate means, and connected to a fluid conduit means which can be fluidly communicated to a collection cylinder which is at atmospheric pressure.

15. The device of claim 1 wherein the pressurized air source includes means for regulating pressurized air and means for adjusting pressurization of air.

16. An apparatus for soil desorption procedures comprising:
    a tubular cylinder;
    top and bottom plates secured over opposite open ends of the cylinder;
    sealing gaskets between the top and bottom plates and the opposite open ends of the cylinder;

means connected between the top and bottom plates to hold the plates in compression to the cylinder;

a plurality of holes in the bottom plate aligned with one of the open ends of the cylinder;

a thin nylon membrane means positionable between the holes in the bottom plate and the cylinder, the nylon membrane means providing low impedance, high rate water flow while maintaining sufficient pressure differentials for soil desorption over a wide range of pressures;

a channel through the top plate for communication of a high pressure source to the cylinder;

valve means for opening and closing the channel; and collection means operatively attachable to the apparatus beneath the bottom plate for collecting desorped liquid, the collection means including means to maintain the collection means at atmospheric pressure.

17. The means of claim 16 wherein the nylon membrane contains pores having pore diameter sizes ranging form 0.22 micrometers to 5.0 micrometers.

18. The means of claim 16 wherein the thickness of the nylon membrane is approximately 120 micrometers.

19. The means of claim 16 wherein a spacer means is inserted between the nylon membrane means and the bottom plate for spacing the nylon membrane from a container in the cylinder soil sample, the holes being communicable with atmospheric pressure so that the bottom of the nylon membrane is at atmospheric pressure, whereas the top of the nylon membrane is at a positive pressure potential.

20. An apparatus for soil desorption procedures comprising:

a pressure cell adapted to hold a soil sample containing sorbed water;

pressurized air supply manifold in fluid communication between a pressurized air source and the pressure cell;

liquid collection means positioned beneath the pressure cell for collecting any water passing from the pressure cell, the liquid collection means including means for maintaining the liquid collection means at atmospheric pressure;

pressure regulation means for regulation of air pressure to the supply manifold;

valve means for independently opening and closing the fluid communication of the manifold to the pressure cell;

pressure monitoring means for continuously detecting the pressure int he manifold;

the pressure cell including a hollow cylinder into which can be placed a soil sample, means to secure top and bottom plates over opposite open ends of the cylinder, a plurality of apertures through the bottom plate, elastomeric gasket means to providing a fluid seal between the top and bottom plates and opposite ends of the cylinder, and a thin nylon membrane between the soil sample and the apertures of the bottom plate.

21. The means of claim 20 further comprising a plurality of pressure cells each in fluid communication with the pressurized air supply manifold, the valve means including valves to control fluid communication form the manifold to each pressure cell, and a sub-set valve to control fluid communication form the manifold to any two or more of the plurality of pressure cells comprising a set of pressure cells.

22. The means of claim 21 further comprising a plurality of sets of pressure cells.

23. The means of claim 20 further comprising pressure transducer means operatively connectable to each liquid connection means for detecting pressure due to liquid collection means and creating a signal corresponding to that difference.

24. The device of claim 23 further comprising the processing means for receiving the signal from the pressure transducer means and utilizing that signal to calculate the amount of fluid in the fluid container at a given time.

25. The means of claim 24 wherein the processing means further comprises means to correlate the amount of liquid in the container with the amount of pressure in the corresponding cell to derive soil characteristics.

26. A method of soil desorption comprising in the steps of:

hydrating a soil sample;

placing the soil sample in abutment with a thin nylon membrane means for providing low impedance, high rate water flow while maintaining sufficient pressure differentials for soil desorption over a wide range of pressures in a substantially sealed container;

creating a superatmospheric pressure potential between the soil sample and the side of the nylon membrane opposite to the side abutting the soil sample, where the superatmospheric pressure potential is created between the container holding the soil sample and the opposite side of the nylon membrane which is at atmospheric pressure;

increasing the high pressure potential to urge any free water in or around the soil sample out of the soil sample and through the nylon membrane;

increasing the high pressure potential incrementally for adsorbed and absorbed water in the soil sample from the soil sample through the membrane;

correlating the amount of water forced through the membrane to the corresponding high pressure potential.

27. The method of claim 26 wherein the soil sample was hydrated as a result of its natural state.

28. The method of claim 26 wherein the soil sample is hydrated artificially.

29. The method of claim 26 wherein correlation of the amount of water forced through the membrane to the corresponding high pressure potential is utilized to derive soil characteristics of the soil sample.

* * * * *

UNITED STATES PATENT AND TRADEMARK OFFICE
CERTIFICATE OF CORRECTION

PATENT NO. : 5,161,407

DATED : November 10, 1992

INVENTOR(S) : Mark D. Ankeny, et al

It is certified that error appears in the above-indentified patent and that said Letters Patent is hereby corrected as shown below:

On the title page item [73], delete "Iowa State University Research Foundation, Inc., Ames, Iowa" and substitute --Assignees: Iowa State University Research Foundation, Inc., Ames, Iowa; and the United States of America.--.

Signed and Sealed this

Nineteenth Day of September, 1995

Attest:

BRUCE LEHMAN

*Attesting Officer*          *Commissioner of Patents and Trademarks*